United States Patent [19]

Jessel, Jr. et al.

[11] Plant 4,556

[45] Jun. 24, 1980

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 14,501

[22] Filed: Feb. 23, 1979

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Donald D. Jeffery

[57] ABSTRACT

A chrysanthemum plant known by the cultivar name Butterball and particularly characterized as to uniqueness by the combined characteristics of flat capitulum form; pompon capitulum type; dark yellow ray floret color; diameter across face of capitulum ranging from 40 to 45 mm. at maturity; uniform eight week photoperiodic flowering response to short days; tall plant height when grown as a pinched spray pot, and semi-upright branching pattern.

6 Drawing Figures

The present invention comprises a new and distinct cultivar of *Chrysanthemum morifolium*, Ramat., hereinafter referred to by the cultivar name Butterball.

Butterball is a product of a planned breeding program which had the objective of creating new chrysanthemum cultivars with pompon capitulum type, with yellow or white ray floret color, with eight or nine week flowering response, and with the ability to produce commercially acceptable quality in year round pot mum programs. Such traits in combination were not present in previously available commercial cultivars.

Butterball was originated from a cross made in a controlled breeding program in Barberton, Ohio in 1974. The female parent was Pearls, disclosed in U.S. Plant Pat. No. 3,970, a white pompon. The male parent of Butterball was #70293005 (unnamed seedling), a yellow pompon originated by the present inventors from a cross between Iceberg (unpatented; commercially available) and Polaris (unpatented; commercially available). Iceberg is a product of the breeding program of the present inventors. Polaris is of parentage unknown to the present inventors.

Butterball was discovered and selected as one flowering plant within the progeny of the stated cross by Walter H. Jessel, Jr. and William E. Duffett on Nov. 17, 1975 in a controlled environment in Barberton, Ohio.

The first act of asexual reproduction of Butterball was accomplished when vegetative cuttings were taken from the initial selection in February, 1976 in a controlled environment in Barberton, Ohio, by a technician working under formulations established and supervised by Walker H. Jessel, Jr. and William E. Duffett. Continued asexual reproduction by vegetative cuttings for evaluative tests in flowering and stock programs in conjunction with horticultural examination of selected units initiated May 31, 1977 has demonstrated that the combination of characteristics as herein disclosed for Butterball are firmly fixed and are retained through successive generations of asexual reproduction.

Butterball has not been observed under all possible environmental conditions. The phenotype may vary significantly with variations in environment such as temperature, light intensity, and daylength. The following observations, measurements, and comparisons describe plants grown in Barberton, Ohio and Salinas, Calif. under greenhouse conditions which approximate those generally used in commercial practice. The following traits have been repeatedly observed and are determined to be basic characteristics of Butterball which in combination distinguish this chrysanthemum as a new and distinct cultivar:

(1) Flat capitulum form.

(2) Pompon capitulum type.

(3) Dark yellow ray floret color, with minimal color oxidation.

(4) Diameter across face of capitulum ranging from 40 to 45 mm. at maturity.

(5) Uniform eight week photoperiodic flowering response to short days.

(6) Tall plant height (requiring 1–2 long day weeks prior to pinch and short days, and two applications 2500 ppm B-9 SP 14 to 21 days after the beginning of short days to attain a flowered plant height of 30 to 45 cm.).

(7) Semi-upright branching pattern.

The accompanying photographic drawings show typical inflorescence and foliage characteristics of Butterball, with colors being as nearly true as possible with illustrations of this type. Sheet 1 is a color photograph of the inflorescence of Butterball. Some difficulty was encountered in obtaining accurate ray floret color representation, with the depicted color being more red (gold) than the actual ray floret color. The color readings stated within the following description are, however, correct. Sheet 2 is a black and white photograph showing three views of the capitulum of Butterball. Sheet 3 is a black and white photograph of the foliage of Butterball at three states of growth.

Of the many commercial cultivars known to the present inventors, the most similar in comparison to Butterball are Sunny Mandalay, disclosed in U.S. Plant Pat. No. 3,231, and the parental cultivar Pearls. Reference is made to attached Chart A which compares certain characteristics of Butterball to those same characteristics of Sunny Mandalay and Pearls. General comparisons are as follows:

(1) In comparison to Sunny Mandalay, Butterball has different capitulum form, different capitulum type, more upright branching pattern, smaller diameter across face of capitulum, taller plant height, and shorter flowering response period. The ray floret color of Butterball is similar to the ray floret color of Sunny Mandalay.

(2) In comparison to Pearls, Butterball has different (dark yellow) ray floret color, more upright branching pattern larger diameter across face of capitulum, taller plant height, and longer flowering response period. The capitulum form and capitulum type of Butterball are similar to those same characteristics of Pearls.

In the following description, color references are made to A Limit Color Cascade, by the Munsell Company, 1972 edition. The color values were determined between 10:00 and 10:30 A.M. on Nov. 16, 1978 under 100 foot-candle light intensity at Salinas, Calif.

Botanical classification: *Chrysanthemum morifolium,* Ramat., cv Butterball.

INFLORESCENCE

A. Capitulum:
- *Form.*—Flat.
- *Type.*—Pompon.
- *Diameter across face.*—40 to 45 mm.

B. Corolla of ray florets:
- *Color (general tonality).*—Dark yellow, 26-5.
- *Color (abaxial).*—21-5 (immature) to 26-5 to 26-4 (mature).
- *Color (adaxial).*—26-3.
- *Persistence.*—Resists shatter.

C. Reproductive organs:
- *Androecium.*—Present disc florets only; scant to few; scant pollen.
- *Gynoecium.*—Present both ray and disc florets.

PLANT

A. General appearance:
- *Branching pattern.*—Semi-upright.
- *Height.*—Tall (pot culture); responsive to B-9 SP for height control.

B. Foliage:
- *Color (abaxial).*—Approximately 20-14.
- *Color (adaxial).*—Approximately 20-13 overlaid with white.

CHART A

COMPARISON OF BUTTERBALL, SUNNY MANDALAY AND PEARLS.

| CULTIVAR | RAY FLORET COLOR | CAPITULUM FORM AND TYPE | BRANCHING PATTERN |
|---|---|---|---|
| Butterball | Dark Yellow | Flat pompon | Semi-upright |
| Sunny Mandalay | Dark Yellow | Semi-incurved Decorative | Semi-spreading |
| Pearls | White | Flat pompon | Spreading |

| CULTIVAR | DIAMETER ACROSS FACE OF CAPITULUM | PLANT HEIGHT | FLOWERING RESPONSE PERIOD |
|---|---|---|---|
| Butterball | 40 to 45 mm. | Tall | 8 week |
| Sunny Mandalay | 85 to 100 mm. | Medium | 10 week |
| Pearls | 20 to 25 mm. | Short | 7 week |

COMPARISONS MADE OF PLANTS GROWN AS PINCHED SPRAY POTS IN SALINAS, CALIFORNIA.

We claim:

1. A new and distinct cultivar of *Chrysanthemum morifolium,* Ramat., plant as shown and described, known by the cultivar name Butterball and particularly characterized as to uniqueness by the combined characteristics of flat capitulum form; pompon capitulum type; dark yellow ray floret color, with minimal color oxidation; diameter across face of capitulum ranging from 40 to 45 mm. at maturity; uniform eight week flowering response; tall plant height, and semi-upright branching pattern.

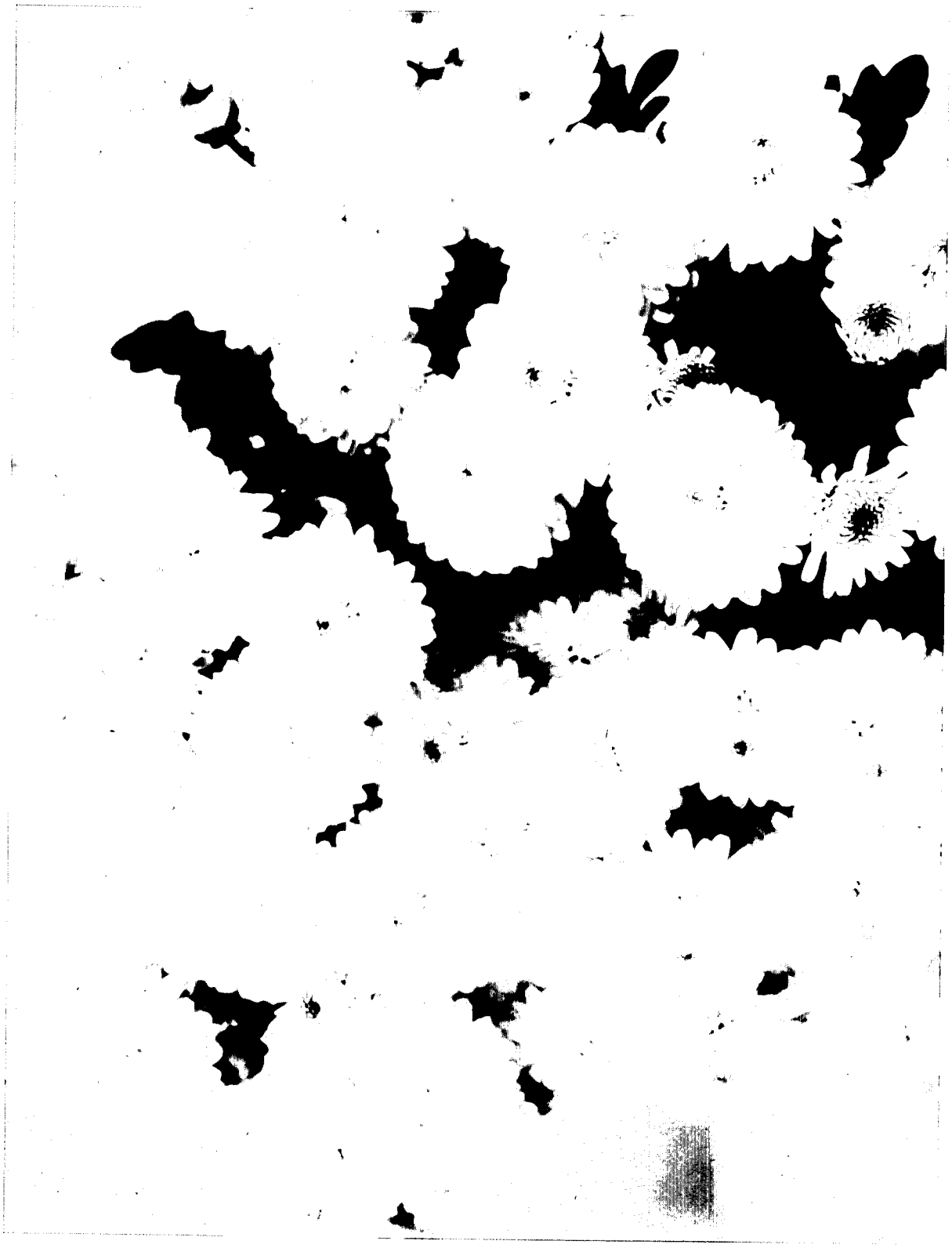

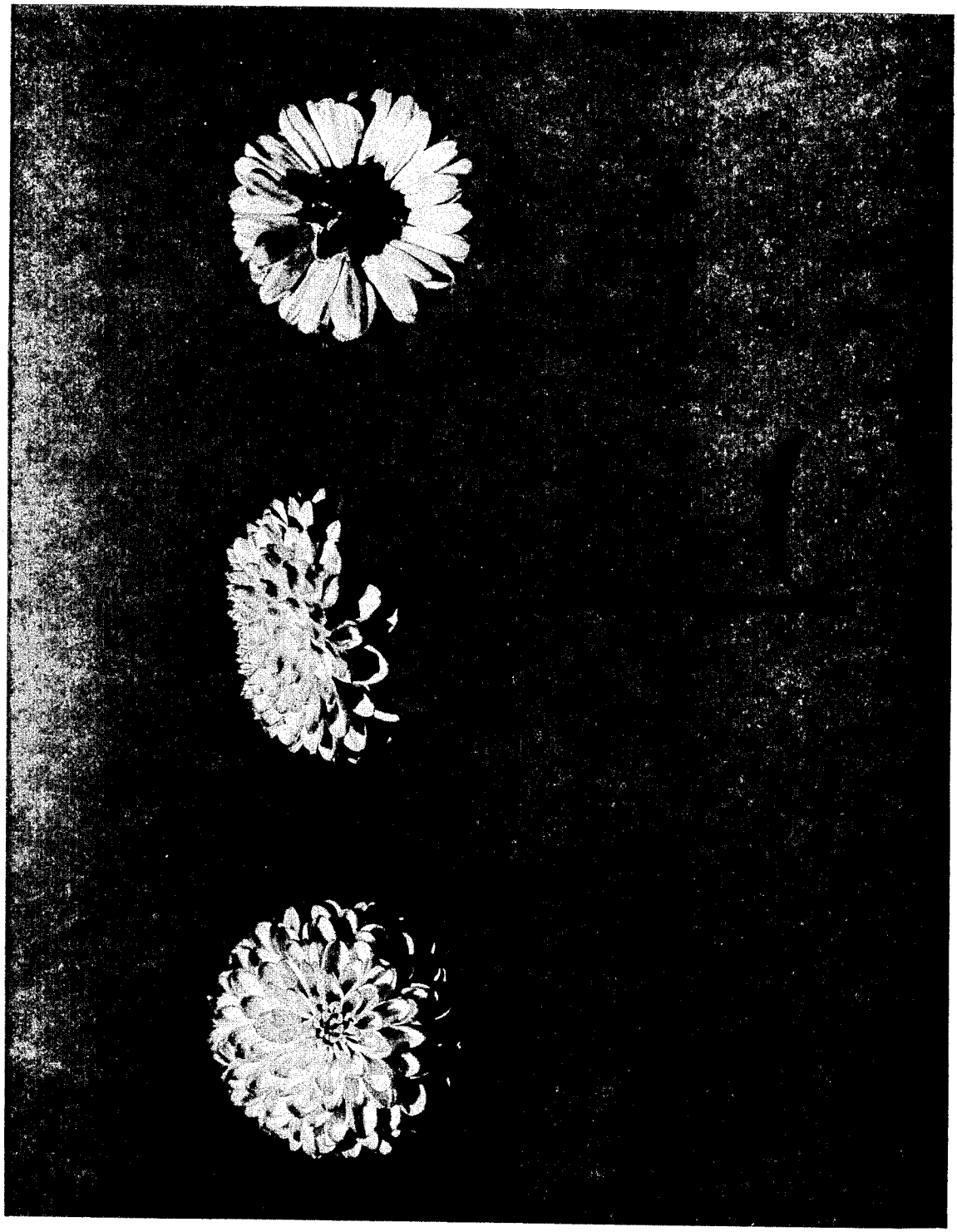

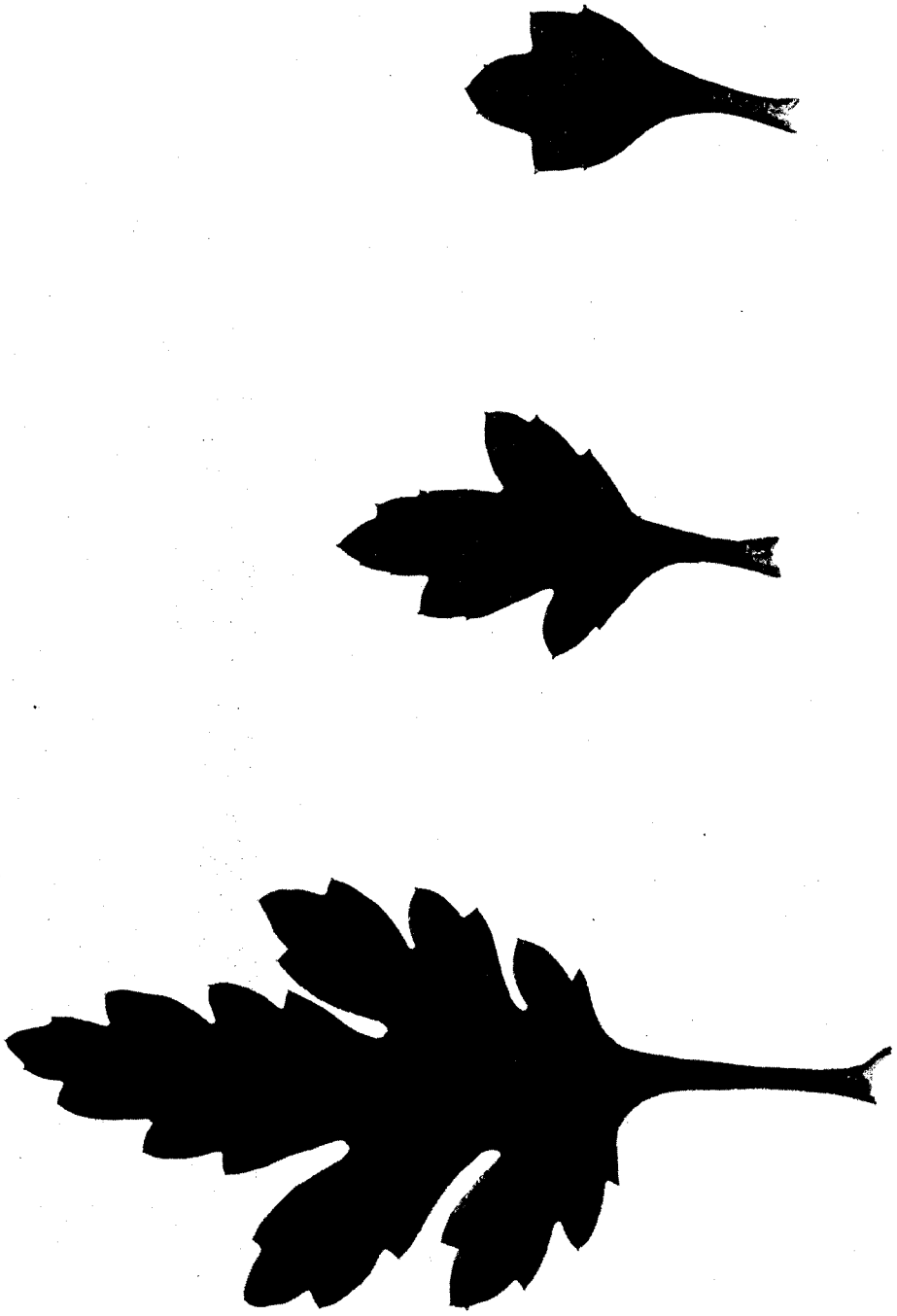

* * * * *